United States Patent [19]

Sudoma

[11] Patent Number: 4,956,295

[45] Date of Patent: Sep. 11, 1990

[54] STABILIZATION OF DRIED BACTERIA EXTENDED IN PARTICULATE CARRIERS

[75] Inventor: A. Louis Sudoma, Milwaukee, Wis.

[73] Assignee: Chr. Hansen's Laboratory, Inc., Milwaukee, Wis.

[21] Appl. No.: 43,105

[22] Filed: Apr. 27, 1987

Related U.S. Application Data

[63] Continuation-in-part of Ser. No. 612,324, May 21, 1984, abandoned.

[51] Int. Cl.$^5$ .................... C12N 1/20; C12N 1/04; C12R 1/23; C12R 1/25
[52] U.S. Cl. ...................... 435/252.1; 435/252.9; 435/260; 435/854; 435/857; 426/61
[58] Field of Search ................ 435/252.9, 260, 854, 435/857; 426/61

[56] References Cited

U.S. PATENT DOCUMENTS 4,205,132  5/1980  Sandine et al. ............... 435/260
4,518,696  5/1985  Gehrman et al. ............. 435/253

OTHER PUBLICATIONS

DeSilva et al., *J. Food Protection*, 46:699–701, (Aug. 1983).
Trollope, D. R.; *J. Appl. Bact.*, 38:115–120, (1975).

*Primary Examiner*—Elizabeth C. Weimar
*Attorney, Agent, or Firm*—Tilton, Fallon, Lungmus & Chestnut

[57] ABSTRACT

Dried viable bacteria are admixed in a particulate carrier composed primarily of an inorganic salt of low moisture absorbing capacity together with a minor proportion of a silica gel absorbent. The inorganic salts may be sodium or calcium carbonates, bicarbonates, sulfates, or phosphates. The admixtures are storable without refrigeration.

15 Claims, No Drawings

STABILIZATION OF DRIED BACTERIA EXTENDED IN PARTICULATE CARRIERS

RELATED APPLICATION

This application is a continuation-in-part of co-pending application Ser. No. 612,324 filed May 21, 1984 now abandoned.

FIELD OF INVENTION, BACKGROUND, AND PRIOR ART

The field of this invention relates to the stabilization of dried bacteria against loss of viability during non-refrigerated storage prior to use. More particularly, the invention is concerned with the stabilization of dried bacteria dispersed in particulate carriers.

Living bacteria have heretofore been combined with particulate carriers to provide admixtures which may be stabilized and stored. See, for example, U.S. Pat. Nos. 3,677,898 (Jeffreys), 3,898,132 (Hettrick), and 4,229,544 (Haynes, et al). Jeffreys describes the coating of lactic acid bacteria with an acetylated monoglyceride, and the combining of the coated bacteria with a starch or sugar carrier mixture which may contain minor amounts of inorganic salts. Hettrick mixes bacteria in aqueous dispersions with diatomaceous earth particles to produce a storable dormant mixture. Haynes, et al. combines bacteria with a carrier such as peat prior to packaging of the bacteria. Particulate desicants have been proposed for use in the freeze-drying of bacteria, as disclosed in U.S. Pat. Nos. 2,853,797 and 2,897,600, but not for admixture with carrier diluents.

Other relevant prior art includes U.S. Pat. Nos. 4,205,132 (Sandine, et al.), 4,518,696 (Gehrman, et al.), 4,115,199 (Porubcan, et al.), 3,897,307 (Porubcan, et al.), 3,616,236 (Delin), 1,957,555 (Reichel et al.), and Hunt et al., "Preservation of Cultures by Drying on Porcelin Beads", *J. of Bacteriology*, Vol. 76, pp. 453–454, 1958, De Silva, et al. "Preservation of Lactic Acid Bacteria on Anhydrous Silica Gel for Three Years", *J. Food Protection*, Vol. 46, pp. 699–701, August, 1983, Trollope, "The Preservation of Bacteria and Fungi on Anhydrous Silica Gel: an Assessment of Survival Over Four Years", *J. appl. Bact.*, Vol. 38, pp. 115–120, 1975.

Sandine et al. describes a method of stabilizing freeze-dried viable bacteria, such as lactic acid producing bacteria in combination with inorganic buffering salts which increase the rate of survival of the bacteria. The bacteria is mixed with a small amount of an alkali metal salt of glycerophosphate in an aqueous medium including milk solids with a pH between 6 and 8. The mixture is frozen and vacuum sealed with the introduction of argon to provide an essentially oxygen-free environment. About 10% of the bacteria surviving lyophilization remain viable for 90 days.

Gehrman et al. describes a stabilized liquid bacterial composition for use as a drench for administration to animals. Porubcan '307 describes the use of dried cultures of lactic acid producing bacterial cells combined with ascorbates, glutamate or aspartate.

De Silva et al. suggests that lactic acid producing bacteria may be effectively stored for long periods of time when in combination with silica gel particles which act as desiccants at low temperatures. Cultures can be stored at 5° C. for four years.

Trollope reports that bacteria tend to survive preservation on silica gel better after drying or lyophilization. Delin describes the procedure for drying mixed Rhizobium strains of nitrogen-fixing bacteria to destroy the weaker strains. A variety of different drying procedures are described. These include the use of desiccants and various heat drying procedures. The drying procedures are to be carried out at a high temperature so that bacteria are killed. The reference states: "Preferably, at least 90% of the bacteria are killed in the course of each drying treatment."

Reichel et al. describes the preparation of neutralized concentrates of Lactobacilli. Neutralizing/buffering agents are added to the moist bacterial concentrates. Preferred additives are milk and milk of magnesia. The resulting product is "a thick viscous liquid which contains a Lactobacilli in the form of a stable concentrate."

Hunt et al. describes a method of preserving bacterial cultures by during on porcelain beads. A liquid broth culture is applied to the beads and thereafter subjected to a drying atmosphere. The atmosphere (not the beads) is in contact with a drying agent, such as silica gel. The bacteria do not contact the silica gel. The reference teaches that such contact is undesirable, stating that the porcelain beads are used "to prevent the contact of the cells with the silica gel which we have found to be deleterious."

As illustrated by some of the foregoing disclosures, the bacteria being stabilized may be intended for a variety of uses in which dilution or extension of a bacterial concentrate is advantageous. The dry bacteria mixtures may be useful in making fermented dairy products, or they may comprise rumen bacteria for feeding to cattle or sheep. They may also be soil bacteria for addition to agricultural soils, or for other purposes.

An important use has developed for *Lactobacillus plantarum* in producing silage fermentation. *Lactobacillus acidophilus* is being extensively used with domestic animals to improve their health and well being. In preparing the Lactobacillus for inoculation of silage, and/or for feeding to domestic animals, it is convenient to have the bacteria in highly diluted form, viz. extended in a particulate carrier which is in dry free-flowing condition. But the diluted bacteria must maintain a high degree of stability under non-refrigerated storage conditions for a number of months prior to use. Heretofore the stabilities of lactic acid bacteria in such dispersions have depended on the dry carrier used and the packaging. Results have often been inconsistent with the lactic acid bacteria showing good stability in some dry carriers and poor stability in others. Unpredictable results have been obtained where the same dry carrier that showed good stability at one time later produced poor stability.

No satisfactory method has been known for producing consistent, reproducible stabilization of bacteria in dry carriers. From a practical standpoint, the problem has been further complicated by observations that greater instability, and greater uncertainty of results occur as the degree of dilution of the bacteria is increased. Yet this is exactly the type of formulation most desired for the large scale uses like those of *L. plantarum* and *acidophilus* referred to above. Prior art disclosures describe the survivability of lactic acid bacteria at low or room temperature. However, the amount of bacteria surviving extended storage periods is relatively small, especially at room temperature. None of the prior art disclosures previously described disclose methods to stabilize bacteria for extended periods of time while maintaining the viability of the bacteria, i.e., large number of the bacteria to function as inoculates of animal feed.

Concentrated cultures of lactic acid producing bacteria may be prepared by the method of U.S. Pat. No. 4,115,199. Tripolyphosphate and/or hexametaphosphate are added to the culture medium prior to separation of the cells by centrifugation. The resulting concentrates have usually been frozen with liquid nitrogen for use in manufacturing cheese or other dairy products. However, sufficient stabilization for distribution in a dry non-refrigerated form can be obtained by the method described in U.S. Pat. No. 3,897,307. The cell culture is adjusted to a pH favorable to the stability of the cells on drying, and chemical stabilizers are added comprising an ascorbate compound together with either a glutamate compound or an aspartate compound (viz. ascorbic acid with monosodium glutamate). The bacteria are then dried by a suitable procedure; viz. freeze-drying, spray drying or fluid bed drying. Drying to a low moisture content, such as 2.5 to 3.5% by weight, is desirable. Good stability is obtained when the product is packaged in moisture impervious containers. This permits non-refrigerated storage and distribution for uses such as home manufacture of yogurt. Such stabilization procedures, however, have not been adequate where the bacteria are mixed with relatively large amounts of particulate carriers to form highly extended bacterial admixtures, such as for addition to animal feeds or addition to silage materials.

SUMMARY OF INVENTION

The present invention is concerned with the combination of dried viable bacteria with particulate carriers to form highly diluted admixtures. The degree of dilution of the bacteria on a weight basis is typically from 1:10 to 1:100,000. To achieve non-refrigerated storability of such dilute admixtures, it has been found that the particulate carrier must be selected in relation to its capacity for adsorbing water. The diluting carrier should have a relatively low water adsorbing capacity, such as less than one percent (1%) of its moisture free weight when equilibrated in air of 50% relative humidity. Carriers of this low water adsorbing character are used in admixture with a minor proportion of a silica gel adsorbent. The silica gel adsorbent is selected to have a high water adsorbing capacity. In general, the adsorbent should be capable of adsorbing at least 10% of its moisture free weight when equilibrated in air at 50% relative humidity. In preferred embodiments, the silica gel adsorbent is selected so that it will adsorb at least 20% of its moisture free weight when equilibrated in air at 50% relative humidity. Given the conditions specified, silica gel-carrier salt admixture can be employed for the dilution of dry bacteria while achieving storable blends that can be packaged in flexible containers, such as laminate-type bags, and distributed and used without refrigeration. The bag laminate should have a low moisture vapor transmission rate (MVTR).

DETAILED DESCRIPTION

The diluent carrier salt should be in finely divided condition, and should be dry and free-flowing. For most purposes, it is important to employ carriers salts which are non-toxic, and which can safely be administered to animals or used as ingredients of animal or human foods. A number of common inorganic salts have been found particularly desirable, such as the sodium, potassium or calcium carbonates, bicarbonates, sulfates, and phosphates. Calcium carbonate and sodium sulfate are advantageous for all around use. Such particulate carrier salt have very low water adsorbing capacity, adsorbing less than 1% of their moisture free weight when equilibrated in air of 50% relative humidity.

The suitability of a diluting carrier salt for the purpose of this invention can be readily determined by performing moisture equilibration tests. The preferred carrier salts are those which adsorb less than 0.3% of their moisture free weight when equilibrated in air at 50% relative humidity, while carrier salt should be rejected for use if they adsorb more than 1% of their moisture free weight under the same relative humidity condition. A further consideration is the water activity of the carrier in its usual commercial form, as available for use in the present invention. It is preferred to employ carrier salts having initial water activities of 0.30 or lower.

The carrier salt of limited water adsorption capacity, as described above, is used in combination with a minor proportion of a silica gel adsorbent. At least 3 parts by weight of the carrier are preferably employed per part of the adsorbent, that is, 75% by weight or greater of the bacterial admixture will comprise the carrier salt. In typical embodiments, as little as 5 parts or less of the silica gel sieve adsorbent are blended per 95 parts or more of the diluting carrier. The blend will therefore comprise at least 95% by weight of the carrier.

Silica gel adsorbents are produced by fine grinding of gelled silicon dioxide ($SiO_2$) The adsorbent particles are amorphous, porous, and have a high affinity for water vapor. Silica gel adsorbents are available commercially having varying capacities for adsorbing water vapor. For the purposes of this invention, the silica gel adsorbent should be selected so that it has a water adsorbing capacity of at least 10% of its moisture free weight when equilibrated in air at 50% relative humidity. For optimized performance, a silica gel adsorbent is preferably selected which is capable of adsorbing 20% of its moisture free weight when equilibrated in air at 50% relative humidity. One preferred class of silica gel adsorbents are sold under the trademark name "Syloid" silicas by the Davison Chemical Division of W. R. Grace & Co., Baltimore, Maryland. Specifically desirable "Syloid" silica gels are sold by this company under the names "Syloid 63", "Syloid 63 FP" and "Syloid AL-1". However, silica gel adsorbents obtainable from other sources can be used provided they meet the water adsorbing criteria set out above.

The method of this invention can be applied to any dry viable bacteria. After culturing the bacteria according to known procedures, they can be separated from the fermentation media by the method described in U.S. Pat. No. 4,115,199, which in that patent is directed particularly to the recovery of lactic acid producing bacteria. The separation of the media constituents is promoted by adding to the fermentation media from 0.25 to 5.0% based on the weight of the complete culture of tripolyphosphate or a hexametaphosphate containing from 4 to 22 phosphate groups. For example, sodium hexametaphosphate or sodium tripolyphosphate may be used in an amount of 0.5 to 4.0% of the culture. Following addition of the phosphate salt, the cells are recovered by centrifugation in a purified, concentrated form. The cells may then be dried by conventional procedures such as freeze-drying (lyophilization) or spray-drying. Before drying, the pH is preferably adjusted to a pH favoring the stability of the cells, such as a pH from about 6.0 to 6.5. Additives may be incorporated to act as anti-oxidants and/or cryoprotectants. Such additives are disclosed in U.S. Pat. No. 3,897,307. The stabilizers may include a combination of an ascorbate compound selected from L. ascorbic acid and the water-soluble salts thereof, and a second stabilizer selected from the class consisting of glutamic acid, aspartic acid, and the water-soluble salts thereof. For most uses, it is preferred to employ non-toxic or edible additives. The amounts of the additives may comprise use of the ascorbate compound equivalent on a molar basis to 4 to 20 parts by weight of L-ascorbic acid, and the glutamate or aspartate additive in an amount equivalent on a molar basis to 1.5 to 20 parts by weight of monosodium glutamate. Further details of preferred procedures are given in the cited U.S. Pat. No. 3,897,307. This patent relates particularly to the preparation of stabilized dry cultures of lactic acid producing bacteria, but the same procedures can be applied to other bacteria.

Prior to freeze-drying, which is a preferred drying procedure, it is desirable to add one or more cryoprotectants. Such cryoprotectants include substances like inositol, sorbitol, mannitol, glucose, sucrose, etc., as disclosed in greater detail in the cited patent.

A preferred subclass of bacteria for use in the present invention is the harmless lactic acid-producing bacteria. These may be Streptococcus, Lactobacillus, Pediococcus or Leuconostoc species. For example, the Streptococcus species may include:

| Streptococcus lactis | Streptococcus faecium |
| Streptococcus cremoris | Streptococcus faecalis |
| Streptococcus diacetylactis | |
| Streptococcus thermophilus | |

The Lactobacillus may include:

| Lactobacillus bulgaricus | Lactobacillus coryniformis |
| Lactobacillus acidophilus | subspec. coryniformis |
| Lactobacillus helveticus | Lactobacillus curvatus |
| Lactobacillus bifudus | Lactobacillus brevis |
| Lactobacillus casei | Lactobacillus buchneri |
| Lactobacillus lactis | Lactobacillus fermentum |
| Lactobacillus plantarum | Lactobacillus viridescens |
| Lactobacillus delbrueckii | Lactobacillus amylovorus |
| Lactobacillus thermophilus | Lactobacillus amylophilus |
| Lactobacillus fermetii | Lactobacillus pentosaceus |

The Pediococcus may include:
Pediococcus cerevisia
Pediococcus acidilactici
Pediococcus pentosaceus
The Leuconostoc species may include:
Leuconostoc cremoris
Leuconostoc dextranicum
Leuconostoc mesenteroides
The invention is also particularly applicable to *Propionibacterium shermanni*.

MANUFACTURING PROCEDURES

In general, the manufacturing operation will comprise the blending of three components: (a) the particulate carrier salt, (b) the silica gel adsorbent, and (c) the dried bacteria. Prior to blending, these ingredients can be maintained in sealed containers in which they are protected from atmospheric humidity. They can therefore be maintained under conditions of low water activity. The freeze-dried bacteria will in general have $a_w$ below 0.10, and the water activity of the silica gel adsorbent can be relatively low, such as 0.03 to 0.04 $a_w$.

In preferred embodiments, only a relatively small proportion of the silica gel adsorbent is needed for use with the carrier salt. For production of a blend having an overall water activity below 0.15, as preferred, such as a water activity in the range of 0.02 to 0.1, a calculation can be made to determine the amount required, depending on the water absorbing capacity of the adsorbent at the desired final $a_w$. In other words, the total amount of water in the carrier is determined, and then the amount of the adsorbent required to adsorb that amount of water is calculated. The resulting blend will then have a final water activity in the desired range. Some excess of the adsorbent may be included to allow for any water vapor which will penetrate the flexible containers in which the stabilized admixtures are to be stored and distributed. For example, the total surface area of the bag may be determined, and from the moisture vapor transmission rate (MVTR) of the package of material, the amount of moisture which can penetrate under conditions of high humidity, such as 90% R.H. at a standard temperature such as 100° F., can be calculated for a selected storage period, such as 1 year. Even with this excess amount, the amount of the adsorbent in the blend is preferably small, such as 1 to 5%.

The blending and packaging operation can be carried out under controlled low humidity conditions, but if this is done with reasonable speed, ordinary atmospheric conditions can be used, such as room temperatures and relative humidities. By carrying out the blending and packaging within periods of 12 to 24 hours, no significant gain in the water activity of the admixture will be produced.

Packaging is preferably in flexible containers, such as laminate-type bags. For example, the bag material may comprise a laminate of paper, aluminum foil, and one or two polyethylene layers. In general, the MVTR of the bag material should be below 0.05, and for optimum results, it should be below 0.005, expressed as $H_2O$ g/100 in$^2$/24 Hr/100° F./90% RH.

The method of this invention is further illustrated by the following specific examples and experimental data.

EXAMPLE I

This example illustrates the preferred mode of practicing this invention, using calcium carbonate as a carrier for *Lactobacillus acidophilus*, and a Syloid silica gel adsorbent.

| 1. Ingredients | Initial $a_w$ |
|---|---|
| Lactobacillus acidophilus | 0.04 |
| Calcium Carbonate | 0.25 |
| Syloid 63 (63 FP, or AL-1) | 0.03 |
| 2. Packaging | Specifications |
| Dimensions | 17 × 24 in. |
| MVTR | .002 g/100 in$^2$/24 Hr/100° F./90% RH |
| Storage | 1 Year |
| Package Size | 50 lbs. |
| 3. Determining Amount of Syloid for Packaging | |
| A. [(17 × 24 in) × (2 sides) × (.002 g)] ÷ 100 in$^2$ = .01632 g H$_2$O vapor penetrated/day | |
| B. (.01632 g H$_2$O) × (365 days) = 5.9548 g H$_2$O vapor penetrated/year | |
| C. (5.9568 g H$_2$O) ÷ (0.07)* = 85.097142 g Syloid 63 needed/50# bag | |

-continued

| 1. Ingredients | Initial $a_w$ |
|---|---|

*Syloid 63, 63FP, or AL-1 adsorbs an average of 7% (.07) H$_2$O)ranging from as little as 2% at 0.10 $a_w$ to 27% at 0.90 $a_w$.
D. (85.097142 g) ÷ [(50 lbs) × (454 g)] = .0037487
E. (.0037487) × (2000 lb. batch) = 7.50 lbs. Syloid 63 needed to compensate for packaging.

4. Determining Amount of Syloid 63 for Calcium Carbonate [(1942.50[1] − S × (.00088)[2]1 ÷ .07[3] = 24.12 lbs. Syloid 63 needed to lower $a_w$ of calcium carbonate to .03$a_w$.
Where: [1]1942.50 lbs [(2000 lbs) − (50 lbs. L.a. + 7.5C lbs. Syloid 63)]
[2]Calcium Carbonate at 0.25 $a_w$ yields .088% (.00088) H$_2$O
[3]Syloid 63, 63FP, or AL-1 adsorbs avg. of 7.0% (.07) H$_2$O 5. Final Formulation

| Ingredients | Lbs/Ton |
|---|---|
| *Lactobacillus acidophilus* | 50.00 |
| Syloid 63, 63FP or AL-1 (7.50 + 24.12) | 31.62 |
| Calcium Carbonate | 1918.38 |

6. Manufacturing Instructions
A. 1st Blend adsorbent into particulate carrier. The length of time is dependent on mixer capacity and type. This water activity conditioning is almost immediate.
B. Blend lactic acid bacteria into the conditioned particulate carrier. Again, time is dependent on mixer capacity and type.
C. Following good manufacturing practices fill and package off as soon as possible using heat-sealing type of packaging equipment. For example, a laminate of paper/polyethylene/aluminum foil/low density polyethylene may be used with specifications: 3 ply 50# Kraft paper/6# PE/1.5 mil foil/ 20# LDPE (Ludlow Packaging, Homer, LA).

EXAMPLE II

This example illustrates the preferred mode of practicing this invention using sodium sulfate as the carrier for *Lactobacillus plantarum*, and a Syloid silica gel adsorbent.

| 1. Ingredients | Initial $a_w$ |
|---|---|
| *Lactobacillus plantarum* | 0.035 |
| Sodium Sulfate | 0.60 |
| Syloid 63 (63 FP, or AL-1) | 0.03 |

2. Packaging

| | |
|---|---|
| Dimensions | 17 × 31 in. |
| MVTR | .0003 g/100 in$^2$/24 Hr./100° F./90% RH |
| Storage | 1 Year |
| Package Size | 60 Lbs. |

3. Determining Amount of Syloid for Packaging
A. [(17 × 31 in) × (2 sides) × (.0003 g)] ÷ 100 in$^2$ = .003162 g H$_2$O vapor penetrated/day
B. (.003162 g H$_2$O) × (365 days) = 1.15413 g H$_2$O vapor penetrated/year
C. (1.15413 g H$_2$O) ÷ (.07)* = 16.487571 g. Syloid 63 needed/60# bag
*Syloid 63, 63FP, or AL-1 adsorbs an avg. of 7% (.07) H$_2$O ranging from as little as 2% at 0.10 $a_w$ to 27% at 0.90 $a_w$.
D. (16.487571 g) ÷ [(60 lbs) × (454 g)] = .0006052.
E. (.0006052) × (2000 lb. Batch) = 1.21 lbs. Syloid 63 needed to compensate for packaging.

4. Determining Amount of Syloid 63 for Sodium Sulfate
A. [(1958.79[1] −S) × (.00132)[2]] ÷ .07[3] = 36.25 lbs. Syloid 63 needed to lower $a_w$ of Sodium Sulfate to .03 $a_w$.
Where: S is amount of Syloid 63, 63FP, or AL-1
[1]1958.79 lbs. [2000 lbs) − (40 lbs. L.p. + 1.21 lbs. Syloid 63)]
[2]Sodium Sulfate at 0.60 $a_w$ yields .132% (.00132) H$_2$O
[3]Syloid 63, 63FP, or AL-1 adsorbs avg. of 7.0% (.07) H$_2$O 5. Final Formulation

| Ingredients | Lbs/Ton |
|---|---|
| *Lactobacillus plantarum* | 40.00 |
| Syloid 63, 63FP or AL-1 (1.21 + 36.25) | 37.46 |
| Sodium Sulfate | 1922.54 |

6. Manufacturing Instructions
The manufacturing and packaging instructions are the same as in Example I, except that the foil layer of the laminate is 3.5 mils to reduce the MVTR.

EXAMPLE III

This example presents the results of experiments demonstrating the value of the present invention in stabilizing dry bacteria extended in particulate carrier salts. The details of the test procedure are summarized below.

1. Particulate Carriers and Conditioning

A. Carriers were chosen which have been typically used as carriers for agricultural-related products, such as sodium sulfate and calcium carbonate.

B. Carrier samples were split (from same lot) conditioning one-half with the silica gel adsorbant. The other half was not subjected to any conditioning (control).

C. The Syloid 63 or AL-1 was added in calculated amounts required to achieve the initial $a_w$ values shown in the tables, the calculations being as illustrated in Examples I and II.

2. Bacterial Additions

Dried lactic acid bacteria (i.e. *L. acidophilus* and *L. plantarum*) were equally added to the control carrier and conditioned carrier. The bacteria had been concentrated and stabilized as described in U.S. Pat. Nos. 4,115,199 and 3,897,307.

3. Blending/Packaging

After thorough blending, 60 gm. of sample were placed in moisture-proof pouches yielding approximately 10–12 pouches for control + 10–12 pouches for conditioned.

4. Testing

After each designated time interval, a pouch from each group was opened, water activities and microbiological platings were run. All pouches were stored at ambient temperature (23° C.). For *L. acidophilus* platings, MRS agar was used and for *L. plantarum* platings, LBS agar was used.

5. Results

The results are summarized in Tables A and B. In all cases, the stability of the bacteria were statistically improved when the water activity was lowered and controlled by addition of the silica gel adsorbent, regardless of the type of carrier used and degree of dilution with the bacteria.

TABLE A

*LACTOBACILLUS ACIDOPHILUS* VS. CARRIERS AT 23° C. STORAGE

| | CALCIUM CARBONATE | | | | SODIUM BICARBONATE | | | |
|---|---|---|---|---|---|---|---|---|
| | CONTROL | | CONDITIONED | | CONTROL | | CONDITIONED | |
| | CFU/gm | aw | CFU/gm | aw | CFU/gm | aw | CFU | aw |
| 0 | $83 \times 10^6$ | .188 | $18 \times 10^7$ | .124 | $26 \times 10^7$ | .234 | $25 \times 10^7$ | .036 |
| 30 | $35 \times 10^6$ | .198 | $15 \times 10^7$ | .038 | $18 \times 10^7$ | .232 | $25 \times 10^7$ | .047 |
| 60 | $10 \times 10^5$ | .315 | $62 \times 10^6$ | .055 | $85 \times 10^6$ | .256 | $19 \times 10^7$ | .073 |
| 90 | $16 \times 10^5$ | .290 | $24 \times 10^6$ | .079 | $44 \times 10^6$ | .289 | $20 \times 10^7$ | .090 |
| 120 | $11 \times 10^5$ | .300 | $20 \times 10^6$ | .045 | $23 \times 10^6$ | .247 | $21 \times 10^7$ | .183 |
| 150 | $27 \times 10^3$ | .356 | $15 \times 10^6$ | .088 | $31 \times 10^5$ | .287 | $15 \times 10^7$ | .102 |
| 180 | $75 \times 10^2$ | .385 | $70 \times 10^5$ | .054 | NA | NA | NA | NA |
| 270 | NA | NA | NA | NA | $76 \times 10^4$ | .262 | $65 \times 10^6$ | .220 |
| 365 | $7 \times 10^1$ | .299 | $26 \times 10^5$ | .181 | $<1 \times 10^2$ | .305 | $18 \times 10^5$ | .271 |

(1) All values expressed as CFU/gm of total mixtures.
(2) NA - Not available.
(3) In order to eliminate any variations in water activity samples were placed in moisture-resistant paper-/foil/poly pouches.
(4) The bacterial concentration in the mixtures was in the range of 0.15 to 0.30 wt. %.

TABLE B

*LACTOBACILLUS PLANTARUM* VS. CARRIERS AT 23° C. STORAGE

| | CALCIUM CARBONATE | | | | SODIUM SULFATE | | | |
|---|---|---|---|---|---|---|---|---|
| | CONTROL | | CONDITIONED | | CONTROL | | CONDITIONED | |
| | CFU/gm | aw | CFU/gm | aw | CFU/gm | aw | CFU/gm | aw |
| 0 | $43 \times 10^8$ | .189 | $45 \times 10^8$ | .074 | $14 \times 10^7$ | .306 | $39 \times 10^7$ | .035 |
| 30 | $28 \times 10^8$ | .258 | $48 \times 10^8$ | .053 | $81 \times 10^5$ | .293 | $38 \times 10^7$ | .037 |
| 60 | $33 \times 10^8$ | .218 | $55 \times 10^8$ | .046 | $69 \times 10^5$ | .274 | $49 \times 10^7$ | .033 |
| 90 | $16 \times 10^7$ | .262 | $28 \times 10^8$ | .090 | NA | NA | NA | NA |
| 120 | $77 \times 10^6$ | .348 | $35 \times 10^8$ | .140 | $54 \times 10^3$ | .276 | $51 \times 10^7$ | .034 |
| 150 | $42 \times 10^4$ | .587 | $20 \times 10^8$ | .201 | NA | NA | NA | NA |
| 180 | $18 \times 10^6$ | .298 | $32 \times 10^8$ | .057 | $52 \times 10^2$ | .244 | $40 \times 10^7$ | .024 |
| 365 | $10 \times 10^6$ | .242 | $28 \times 10^8$ | .050 | NA | NA | NA | NA |

(1) All values expressed as CFU/gm of total mixtures.
(2) NA - Not available.
(3) In order to eliminate any variations in water activity samples were placed in moisture-resistant paper/foil/poly pouches.
(4) The bacterial concentration in the mixtures was in the range of 0.15 to 0.30 wt. %.

While the invention has been described in detail and with reference to specific embodiments thereof, it will be apparent to one skilled in the art that various changes and modifications can be made therein without departing from the spirit and scope thereof.

We claim:

1. The method of forming a stabilized mixture of dried viable bacteria extended in a particulate carrier, comprising:

(a) preparing a blend by intermixing a major proportion of a carrier comprising particulate inorganic salt administrable to animals with a minor proportion of a silica gel adsorbent, said carrier salt being selected to have a water adsorbing capacity of less than one percent (1%) of its moisture free weight when equilibrated in air of 50% relative humidity and being blended in at least 3 parts by weight per each part of said adsorbent, said silica gel adsorbent having a water adsorbing capacity of at least 20% of its moisture free weight when equilibrated in air at 50% relative humidity, said blend containing about 1 to 5% by weight of said adsorbent;

(b) dispersing in said blend either during the intermixing of step (a) or subsequent thereto dried viable bacterial to form a highly diluted storable admixture thereof and (c) packaging said admixture in packaging material having a low vapor transmission rate.

2. The method of claim 1 in which said carrier salt is selected from the class consisting of sodium or calcium carbonates, bicarbonates, sulfates, or phosphates.

3. The method of claim 1 in which said bacteria are harmless lactic acid producing bacteria.

4. The method of forming stabilized admixtures of dried viable harmless lactic acid producing bacteria, comprising:

(a) preparing a blend by intermixing a particulate carrier comprising an inorganic salt administrable to animals with a silica gel adsorbent, said blend containing at least 75% by weight of said carrier salt which has a water adsorbing capacity of less than 0.3 percent of its moisture free weight when equilibrated in air of 50% relative humidity, said silica gel adsorbent being present in said blend in an amount of about 1% by weight and having a water adsorbing capacity of least 20% of its moisture free weight when equilibrated in air at 50% relative humidity; and (b) dispersing in said blend either during the intermixing of step (a) or subsequent thereto said dried viable lactic acid producing bacteria to form a highly diluted storable admixture thereof, said bacteria having been freeze-dried before dispersing in said blend.

5. The method of claim 4 in which said carrier salt is selected from the class consisting of sodium or calcium carbonates, bicarbonates, sulfates, or phosphates.

6. The method of claim 4 in which said bacteria is selected from the class consisting of *Lactobacillus acidophilus* and *Lactobacilllus plantarum.*

7. The method of claim 4 in which said stabilized admixtures contain said viable bacteria in amounts of from about $5 \times 10^{11}$ to $1 \times 10^6$ CFU per gram of said blend.

8. The method of claim 4 in which said carrier salt is calcium carbonate.

9. The method of claim 4 in which said carrier salt is sodium sulfate.

10. The extended stabilized bacterial admixture produced by the method of claim 1.

11. The extended stabilized bacterial admixture produced by the method of claim 4.

12. The method of forming stabilized admixtures of dried viable harmless lactic acid producing bacteria, comprising:

(a) preparing a blend by intermixing a particulate carrier with a silica gel adsorbent, said carrier being selected from calcium carbonate or sodium sulfate, said blend containing at least 75% by weight of said carrier, said adsorbent being present in said blend in an amount of about 1 to 5% by weight and having a water adsorbing capacity of at least 20% of its moisture free weight when equilibrated in air at 50% relative humidity; and (b) dispersing in said blend either during the intermixing of step (a) or subsequent thereto said dried viable lactic acid producing bacteria to form a highly diluted storable admixture thereof, said bacteria having been freeze-dried before dispersing in said blend.

(c) packaging said admixture in packaging material having a low vapor transmission rate.

13. The method of claim 12 in which said bacteria is *Lactobacillus acidophilus.*

14. The method of claim 12 in which said bacteria is *Lactobacillus plantarum.*

15. The extended stabilized bacterial admixture produced by the method of claim 12.

* * * * *